US005234920A

United States Patent [19]
Okita et al.

[11] Patent Number: 5,234,920
[45] Date of Patent: Aug. 10, 1993

[54] ANTIBIOTIC C-7 CATECHOL-SUBSTITUTED CEPHALOSPORIN COMPOUNDS, COMPOSITIONS, AND METHOD OF USE THEREOF

[75] Inventors: Takaaki Okita, Tokyo; Hajime Kamachi, Chiba; Shinji Masuyoshi, Yokohama; Kiyoto Imae, Kawasaki, all of Japan

[73] Assignee: Bristol-Myers Squibb Company, New York, N.Y.

[21] Appl. No.: 799,651

[22] Filed: Jan. 6, 1992

Related U.S. Application Data

[62] Division of Ser. No. 572,517, Aug. 23, 1990, Pat. No. 5,095,012.

[51] Int. Cl.$^5$ ............... C07D 501/46; A61K 31/545
[52] U.S. Cl. ..................... 514/202; 514/206; 540/222; 540/225; 540/227
[58] Field of Search ............... 540/225, 222, 227, 221; 514/202, 206

[56] References Cited

U.S. PATENT DOCUMENTS

| | | | |
|---|---|---|---|
| 4,866,055 | 9/1989 | Kato | 514/206 |
| 4,880,798 | 11/1989 | Kate et al. | 540/227 |
| 5,001,121 | 3/1991 | Ohnishi et al. | 540/227 |
| 5,019,570 | 5/1991 | Arnould et al. | 540/222 |
| 5,075,298 | 12/1991 | Aszódi et al. | 540/222 |
| 5,095,012 | 3/1992 | Okita et al. | 540/222 |

FOREIGN PATENT DOCUMENTS

| | | |
|---|---|---|
| 158289 | 7/1987 | Japan . |
| 161793 | 7/1987 | Japan . |
| 167784 | 7/1987 | Japan . |
| 270589 | 7/1987 | Japan . |
| 284183 | 11/1988 | Japan . |
| 175982 | 7/1989 | Japan . |
| 2134522 | 8/1984 | United Kingdom . |

*Primary Examiner*—Nicholas S. Rizzo
*Attorney, Agent, or Firm*—William T. Han

[57] ABSTRACT

The present invention relates to new cephalosporins of the formula wherein
$R^1$ and $R^2$ are hydrogen or carboxy, with the proviso that both cannot be the same;
$R^3$ is hydrogen or acetyl; and
$R^4$ is a radical selected from the group consisting of in which n is 1 or 2, $R^5$ is hydrogen or acetyl, and $R^6$ is hydrogen, a lower $C_{1-3}$ alkyl, or a radical selected from the group consisting of in which n and $R^5$ are as defined above.

In another aspect, this invention relates to processes for the preparation of the compounds of Formula I, to pharmaceutical compositions containing at least one compound of Formula I, and to intermediates in their preparation.

11 Claims, No Drawings

ANTIBIOTIC C-7 CATECHOL-SUBSTITUTED CEPHALOSPORIN COMPOUNDS, COMPOSITIONS, AND METHOD OF USE THEREOF

CROSS REFERENCE

This application is a divisional application of copending application U.S. Ser. No. 7/572,517 filed Aug. 23, 1990, now U.S. Pat. No. 5,095,012.

BACKGROUND OF THE INVENTION

The field of this invention is cephalosporins which contain carboxy and acetylated or unacetylated dihydroxylphenyl (catechol) moieties on the seven position, their antibiotic use and compositions therefor.

In the antibiotic arts, there has long been a need for new and effective antibiotic compounds. Due to rapid changes in the pathogens, for which treatment with the antibiotic compounds are required, the older and more used antibiotics often become either ineffective or significantly less effective against the pathogens. Effective antibiotics are therefore in constant demand to replace the older and more used antibiotics.

Accordingly, a great many cephalosporin compounds have been synthesized and tested for appropriate antibiotic properties by those in the antibiotic field. Because of the above mentioned long felt need in this art for potent and effective antibiotics, even small improvements or advancements in the art can sometimes be very significant.

DESCRIPTION OF THE RELATED ART

A number of cephalosporin compounds having a dihydroxylphenyl moiety on the seven position have been evaluated for antibiotic properties by those in the art. Also, certain cephalosporin compounds having the dihydroxyphenyl radical on the seven position together with a quarternary ammonium group on the three position have been evaluated.

Patent documents and published patent applications which relate to the above class of cephalosporins are as follows:

(A) Japan Kokai No. 62-167784 (published Jul. 24, 1987) relates to a number of cephalosporin derivatives including, inter alia, those represented by the formula

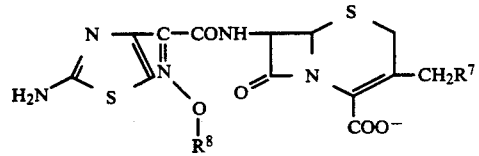

wherein $R^8$ is

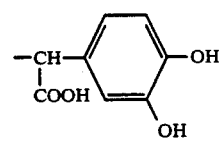

and $R^7$ is

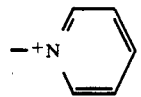

(B) Japan Kokai No. 62-270589 (published Nov. 24, 1987) relates to a number of cephalosporin derivatives including, inter alia, those represented by the formula

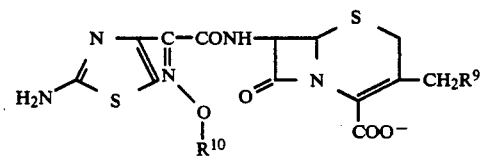

wherein $R^{10}$ is

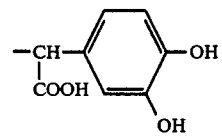

and $R^9$ is

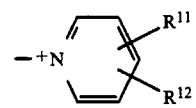

in which $R^{11}$ and $R^{12}$ each are independently hydrogen, —$CO_2H$, —$CONH_2$, alkyl, or $NH_2$, or taken together can be a fused $C_{3-4}$ alkyl.

(C) Japan Kokai Nos. 62-161793 (published 7/17/87) and 1-175982 (published 7/12/89) and U.S. Pat. No. 4,866,055 (issued on 9/12/89 to Kato et al.) disclose a number of cephalosporin derivatives including, inter alia, those represented by the formula

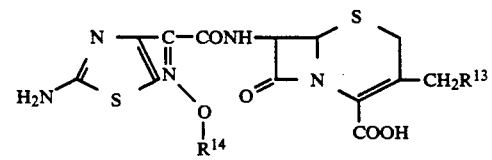

wherein $R^{14}$ is

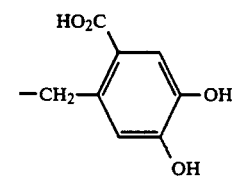

and $R^{13}$ is

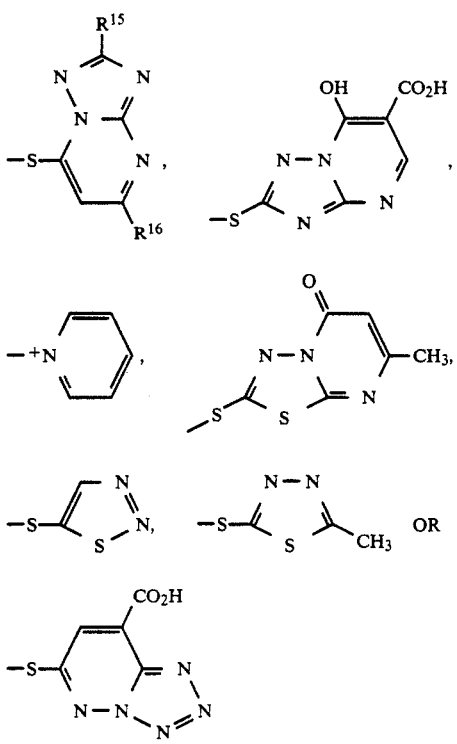

in which $R^{15}$ is —$CO_2H$, H, —$SO_3H$, —$NH_2$, or OH; and $R^{16}$ is H, —$CH_3$, or —$CO_2H$.

(D) Japan Kokai No. 62-158289 (published 7/14/87) relates to, inter alia, cephalosporin derivatives of the formula

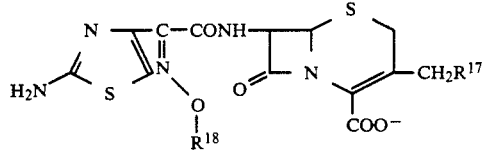

wherein $R^{18}$ is

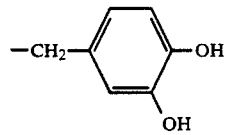

and $R^{17}$ is

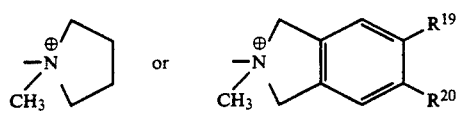

in which $R^{19}$ and $R^{20}$ each are independently hydrogen or hydroxy.

(E) Japan Kokai No. 63-284,183 (published 11/21/88) relates to a number of cephalosporin derivatives including, inter alia, those represented by the formula

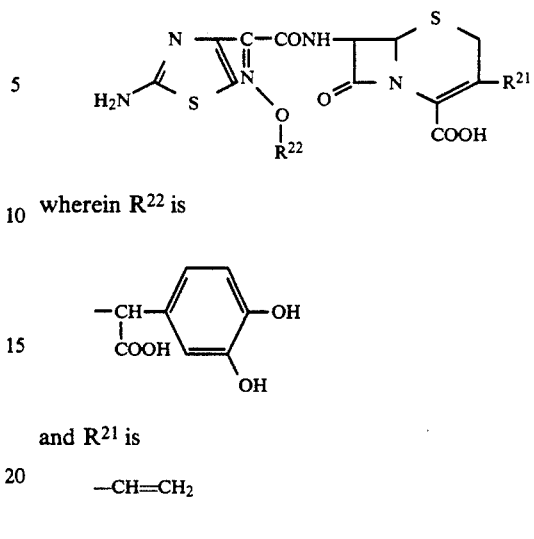

wherein $R^{22}$ is

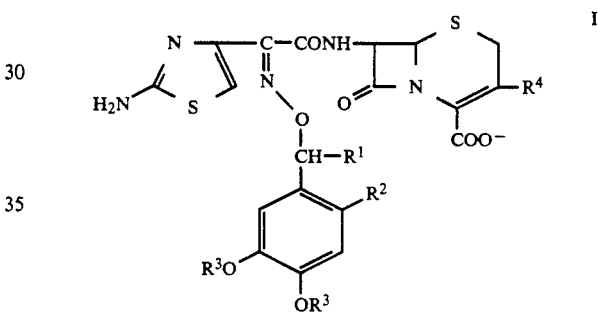

and $R^{21}$ is

—CH=$CH_2$

SUMMARY OF THE INVENTION

This invention relates to novel cephalosporin compounds of Formula I

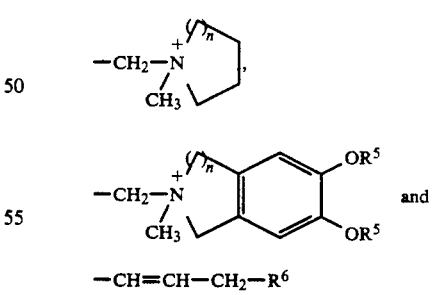

wherein
$R^1$ and $R^2$ are hydrogen or carboxy, with the proviso that both cannot be the same;
$R^3$ is hydrogen or acetyl; and
$R^4$ is a radical selected from the group consisting of

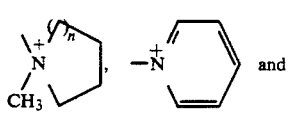

in which n is 1 or 2, $R^5$ is hydrogen or acetyl, and $R^6$ is hydrogen, a lower $C_{1-3}$ alkyl, or a radical selected from -continued

[structure: -N⁺ with ring (n), benzene with OR⁵, OR⁵]

in which n and R⁵ are as defined above.

The compounds of Formula I are potent antibacterial agents.

DETAILED DESCRIPTION OF THE INVENTION

This invention relates to novel antibiotic cephalosporin compounds of Formula I

[structure of Formula I]

wherein
R¹ and R² are hydrogen or carboxy, with the proviso that both cannot be the same;
R³ is hydrogen or acetyl; and
R⁴ is a radical selected from the group consisting of

[structure: -CH₂-N⁺(CH₃) with ring (n)],

[structure: -CH₂-N⁺(CH₃) with benzene OR⁵, OR⁵] and

-CH=CH-CH₂-R⁶ in which n is 1 or 2, R⁵ is hydrogen or acetyl, and R⁶ is hydrogen, a lower $C_{1-3}$ alkyl, or a radical selected from

[structures: N⁺-CH₃ ring, pyridinium] and

[structure: -N⁺ with benzene OR⁵, OR⁵]

in which n and R⁵ are as defined above.

As shown in structural Formula I, the numbering system used for cephalosphorins in this specification follows the most widely used system in the art.

The imino groups in the C-7 side chains of Formula I compounds have either the "syn" (Z) or "anti" (E) configuration. Formula I is drawn as the "syn" isomer. This invention comprises compounds of Formula I containing at least 90% of the "syn" isomer. Preferably the compounds of Formula I are "syn" isomers which are essentially free of the corresponding "anti" isomers.

Furthermore, certain compounds of Formula I and intermediates thereof contain a double bond in the C-3 side chain. The double bond can exit either in the "Z" (cis) or "E" (trans) configuration. The present invention includes compounds of Formula I with the double bonds in both configurations.

Also included within the scope of the invention are the nontoxic pharmaceutically acceptable salts, physiologically hydrolyzable esters or solvates of compounds of Formula I.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula I include $C_{1-6}$ alkyl, benzyl, 4-methoxybenzyl, indanyl, phthalidyl, methoxymethyl, $C_{1-6}$ alkanoyloxy($C_{1-6}$)alkyl, e.g. acetoxymethyl, pivaloyloxymethyl or propionyloxymethyl, $C_{1-6}$ alkoxycarbonyloxy($C_{1-6}$)alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)methyl and other physiologically hydrolyzable esters known and used in the penicillin and cephalosporin arts. Such esters are prepared by conventional techniques known in the art.

The pharmaceutically acceptable acid addition salts of Formula I compounds are those in which anion does not contribute significantly to the toxicity of the salt and are compatible with the customary pharmaceutical vehicles and adapted for oral or parenteral administration. The pharmeutically acceptable acid additions salts include the salts of compounds of Formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-tolenesulfonic acid and other acids known and used in the penicillin and cephalosporin arts. Preparation of these salts is carried out by conventional techniques involving reaction of compounds of Formula I with the acid in a substantially equivalent amount.

Compounds of Formula I also form pharmaceutically acceptable metal and amine salts in which the cation does not contribute significantly to the toxicity or biological activity of the salt. These salts are also part of the present invention. Suitable metal salts include the sodium, potassium, calcium, barium, zinc and aluminum salts. The sodium or potassium salts are preferred. Amine salts prepared from amines used, for instance, with benzyl penicillin which are capable of forming stable salts with the acidic carboxy group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine and dicyclohexylamine.

Further, when a compound of Formula I contains a quarternary ammonio group, it can exit as a zwitterionic form.

Compounds of Formula I exhibit high antibacterial activity against various Gram-positive and Gram-negative bacteria, and are useful in the treatment of bacterial infections in animals, including man. Compounds of Formula I may be formulated for parenteral use in a conventional manner utilizing known pharmaceutical carriers and excipients, and may be presented in unit dosage form or in multidosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. Compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

Compounds of Formula I in which $R^1$ is carboxy and $R^2$ is hydrogen can be prepared by following the steps described below either in Process A or in Process B, or appropriate modifications thereof.

Process A (a) Converting a compound of Formula II

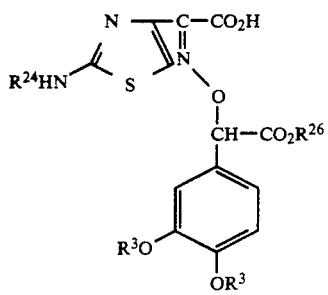

into an acylating acid of Formula III

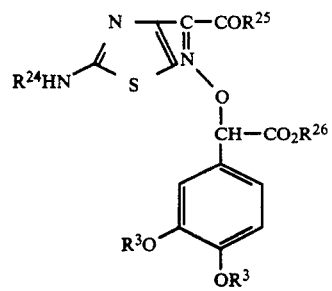

wherein the group represented by —CO $R^{25}$ is an acylating group such as acid halide, mixed acid anhydride, activated ester, and the like. One preferred acylating group is N-hydroxybenzotriazolyl ester. The N-hydroxyenzotriazolyl ester can be prepared by reacting a compound of Formula II with N-hydroxybenzotriazole and dicyclohexylcarbodiimide (DCC). In Formulas II and III, $R^{24}$ is hydrogen or, optionally, a suitable nitrogen protecting group such as trityl (triphenylmethyl); $R^{26}$ is a carboxy-protecting group such as diphenylmethyl (DPM); and $R^3$ is hydrogen or acetyl as defined previously.

(b) Reacting a cephalosporin derivative of Formula IV with a compound of Formula III to afford a compound of Formula V.

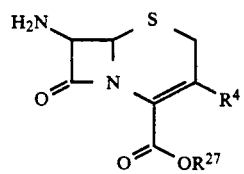

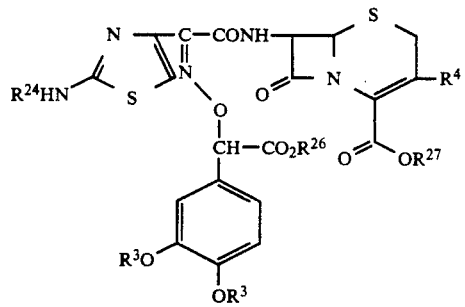

In the above formulas, $R^4$ is as defined previously and $R^{27}$ represents hydrogen, a metal or organic cation, a negative charge, or a carboxy protecting group such as DPM. Compounds of Formula IV with the earlier defined $R^4$ groups can be made by the processes or variations thereof described in the following patents and publications:

U.S. Pat. No. 4,699,979 (issued on 10/13/87 to Hoshi et al.);

U.S. Pat. No. 4,751,295 (issued on 06/14/88 to Oka et al.);

U.S. Pat. No. 4,659,812 (issued on 04/21/87 to Aburaki et al.);

U.S. Pat. No. 4,677,100 (issued on 06/20/87 to Nakagawa et al.); and

Japan Kokai 61-291,429 (published 12/07/86)

(c) Lastly, removing protecting group(s) from a compound of Formula V by a method or combination of methods which includes acid hydrolysis, enzymatic hydrolysis, and the like to afford a desired compound of Formula I.

Process B (a) Reacting a compound of Formula III of Process A with a compound of Formula VI to afford a compound of Formula VII.

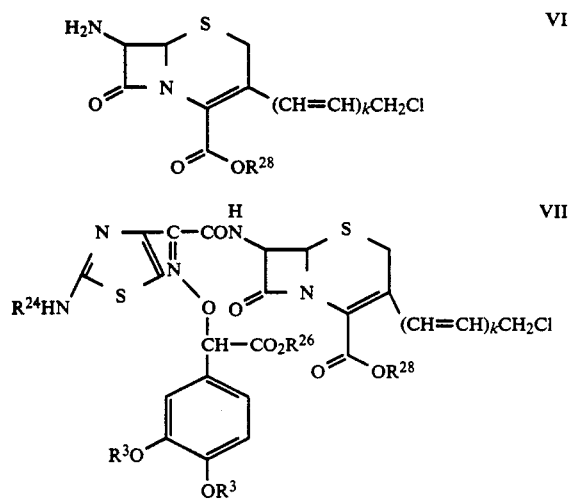

In Formulas VI and VII, k is 0 or 1; $R^{28}$ is a carboxy protecting group, preferably DPM; and $R^{26}$ and $R^{24}$ are as previously defined in Process A. The synthesis of compounds of Formula VI can be accomplished according to the methods described in U.S. Pat. No. 4,751,295 (issued on 6/14/88 to Oka et al.).

(b) Displacing the chlorine atom from a compound of Formula VII by iodine to afford a compound of Formula VIII.

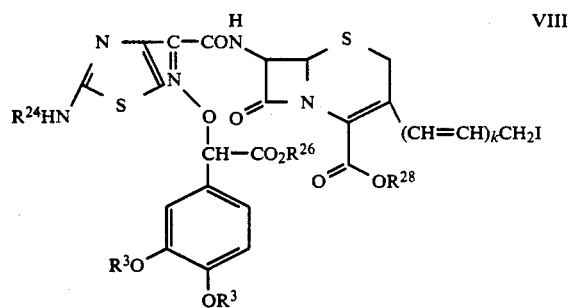

(c) In a compound of Formula VIII, when k equals 0, reacting the compound with amines selected from

and when k equals 1, reacting the compound with amines selected from

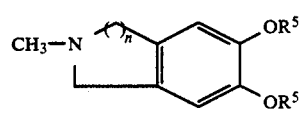

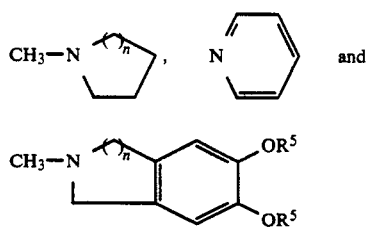

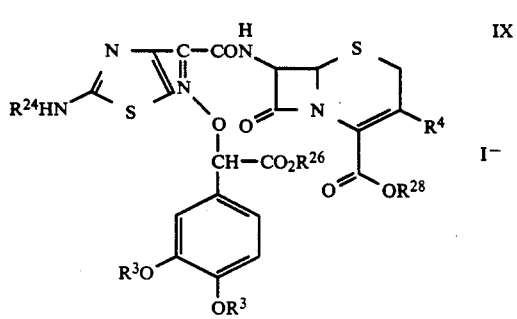

to afford a compound of Formula IX. In the above amines, n and $R^5$ are as defined previously.

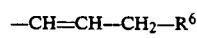

(d) As in Process A, lastly removing protecting group(s) from a compound of Formula IX to afford a Formula I compound.

It shall be understood that Process B is not applicable to making Formula I compounds wherein $R^1$ is carboxy, $R^2$ is hydrogen, and $R^4$ is a radical $$-CH=CH-CH_2-R^6$$

in which $R^6$ is hydrogen or a lower $C_{1-3}$ alkyl.

Preparation of compounds of Formula I, in which $R^1$ is hydrogen and $R^2$ is carboxy group can be prepared by the method which comprises the steps described in Process C below or appropriate modifications thereof.

Process C (a) Converting a carboxy acid of Formula X

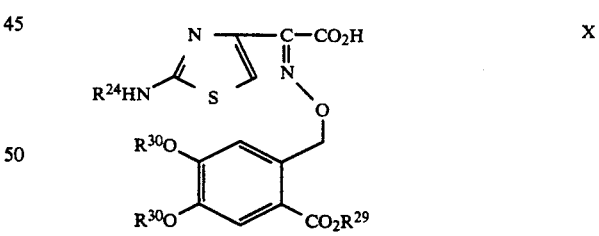

into an activated acid of Formula XI

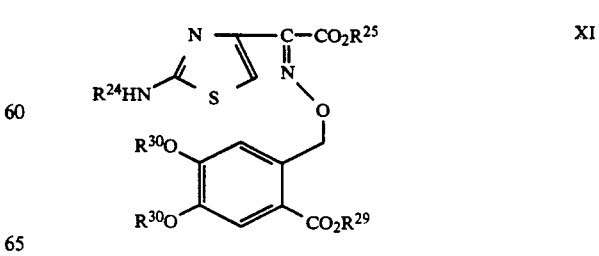

wherein $R^{24}$ is as defined previously in Process A; $R^{29}$ is a carboxy protecting group, preferably t-butyl; $R^{30}$ is a suitable phenol protecting group, preferably two $R^{30}$ taken together form isopropylidene; and as before —$CO_2R^{25}$ is an acylating group such as acid halide, mixed acid anhydride, activated ester, and the like. One preferred acylating group is N-hydroxybenzotriazole ester. The synthesis of the N-hydroxybenzotriazole ester can be accomplished by reacting a compound of Formula X with N-hydroxybenzotriazole and DCC. The starting acid X may be prepared according to the procedure described in Japan Kokai 63-132893 (published 6/4/88).

(b) Reacting a compound of Formula XI with a compound of Formula IV to afford a compound of Formula XII.

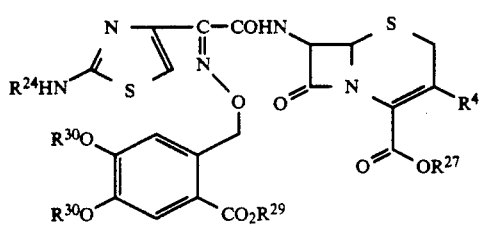

(c) Finally, removing protecting group(s) form a compound of Formula XII to afford a Formula I compound in which $R^1$ is H and $R^3$ is carboxy.

DESCRIPTION OF SPECIFIC EMBODIMENTS

The specific examples and Schemes A, B and C which follow illustrate the synthesis of representative compounds of the instant invention, and are not to be construed as limiting the invention in sphere or scope. The methods disclosed may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-$d_6$ (perdeuterodimethysulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

EXAMPLE 1

Benzotriazol-1-yl 2-(2-aminothiazol-4-yl)-2-(Z)-[diphenylmethyloxycarbonyl(3,4-dihydroxyphenyl)methyl]oxyiminoacetate (IIIa)

A mixture of 2-(2-aminothiazol-4-yl)-2-(Z)-[diphenylmethyloxycarbonyl(3,4-dihydroxyphenyl)methyl]oxyiminoacetic acid (IIa) (779 mg, 1.5 mmol) [for the preparation of compound IIa see: Japan Kokai 88-99078 published 4/30/88], dicyclohexylcarbodiimide (DCC, 352 mg, 1.71 mmol), N-hydroxybenzotriazole (261 mg, 1.71 mmol) in tetrahydrofuran (THF) (6 ml) was stirred at room temperature for 1 hr and the resulting precipitate was filtered off. The filtrate was concentrated under reduced pressure to provide 1.00 gram (100%) of the activated ester IIIa.

IR $\nu_{max}$ (KBr) $cm^{-1}$ 3338, 2932, 1775, 1743, 1618.

EXAMPLE 2

7-[(2-(2-Aminothiazol-4-yl-2-(Z)-[carboxyl(3,4-dihydroxyphenyl)methyl]oxyimino]acetamido]-3-(1-methylpyrrolidinio)-methyl-3-cephem-4-carboxylate (Ia)

To a cooled suspension of 7-amino-3-(1-methylpyrrolidinio) methyl-3-cephem-4-carboxylate hydrochloride (IVa) (558 mg, 1.5 mmol) [for the preparation of compound IVa see: U.S. Pat. No. 4,659,812 issued on 4/21/87 to Aburaki et al.) in DMF (10.8 ml) and $H_2O$ (5.4 ml) was added activated ester IIIa (1.43 g, 2.25 mmol) and the mixture was stirred for four hrs at room temperature, while maintaining the pH of the reaction mixture in a range of five to seven by adding $NaHCO_3$ The reaction mixture was poured into ice water and the precipitate was collected by filtration and dried in vacuo. The solid was dissolved in TFA (10 ml) and anisole (1 ml) and allowed to stand for one hr at ambient temperature. The solution was poured into isopropyl ether with stirring. The product was collected from the resulting suspension and dried. The crude product was purified chromatographically first with Diaion HP-20 and then with Bondapak C-18 to afford 38 mg (4% yield) of the title product, mp. 160 °C. (dec.).

IR $\nu_{max}$ (KBr) $cm^{-1}$ 3387, 1767, 1666, 1612; Ultra Violet Absorption (UV) $\nu_{max}$ (pH 7 phosphate buffer) nm ($\epsilon$) 234 (19,000) 259 (14,300; shoulder); $^1H$ NMR ($D_2O$) $\delta 2.23$ (4H, br s), 2.97 (3H, s), 3.11 (1H, d, J=16.9 Hz), 3.51 (4H, br s), 3.73 (1H, d, J=16.9 Hz), 4.30 (1H, d, J=13.9 Hz), 4.69 (1H, d, J=13.9 Hz), 5.18 (1H, d, J=4.7 Hz), 5.41 (1H, s), 5.74 (1H, d J=4.7 Hz), 6.87–7.07 (3H, m), 7.01 (1H, s); HPLC (column SSC-ODS-262, 254 nm, solvent ten percent $CH_3CN$-pH 3.5 buffer, 1 ml/min): two peaks at 3.13 min and 3.33 min (peak height, ca. 1:1).

EXAMPLE 3

7-[2-(2-Aminothiazol-4-yl)-2-[(Z)-carboxy-(3,4-dihydroxyphenyl)methyl]oxyimino]acetamido]-3-(Z)-1-propenyl]-3-cephem-4-carboxylic acid (Ib)

To a cold mixture of 7-amino-3-[(Z)-1-propenyl]-3-cephem-4-carboxylic acid (IVb) (361 mg, 1.5 mmol) [for the preparation of compound IVb see: U.S. Pat. No. 4,699,979 issued on 10/13/87 to Hoshi et al.] and $Et_3N$ (333 mg, 3.3 mmol) in dry THF (7.2 ml) was added dropwise trimethylsilyl chloride (405 mg, 3.75 mmol) and the mixture was stirred for 30 min at room temperature under argon. Activated ester IIIa (1.00 gram, 1.6 mmol) in DMF (4 ml) was added to the mixture. The suspension was stirred overnight at room temperature and poured into ice water. The resulting precipitate was collected by filtration and dried to give a powdery solid. The powder was dissolved in TFA (10 ml) and anisole (2 ml) and the solution was allowed to stand for thirty min at ambient temperature. The brown solution was poured into isopropyl ether and the precipitate was collected by filtration and dried. The crude product was purified chromatographically by HP-20 (eluent 50% to 60% methanol in water) prior to Bondapak C18 (eluent 20% methanol in water) to yield 136 mg (24% yield) of the title compound, mp 160 °C. (dec.).

IR $\nu_{max}$ (KBr) cm$^{-1}$ 3340, 1765, 1666, 1633; (UV) $\nu_{max}$ (pH 7 phosphate buffer) nm ($\epsilon$) 232 (21,800; shoulder), 285 (16,100); $^1$H NMR (D$_2$O) (some protons show a pair of peaks with the intensity of 1:1 due to the presence of diastereoisomers) δ 1.63 (3H, ddx2, J=1.8 & 7.1 Hz), 3.24 (1H, d, J=18 Hz), 3.53 (1H, d, J=18 Hz), 5.12 & 5.16 (1H, dx2, J=4.7 Hz), 5.31 & 5.32 (1H, sx2), 5.64 (1H, m), 5.68 & 5.70 (1H, ddx2, J=4.7 & 7.7 Hz), 6.13 & 6.15 (1H, ddx2, J=9.8 & 1.8 Hz), 6.67-6.87 (3H, m), 6.87 & 6.86 (1H, sx2), 7.28 (1H, s), 8.99 & 9.00 (1H, sx2), 9.06 & 9.08 (1H, sx2), 9.50 & 9.57 (1H, dx2, J=7.7 Hz); HPLC (column SSC-ODS-262, 254 nm, solvent 15 percent CH$_3$CN-pH 3.5 buffer, one ml/min): two peaks at 7.35 min & 7.99 min (peak height, ca. 1:1).

EXAMPLE 4

7-[(2-(2-Aminothiazol-4-yl)-2-[(Z)-[carboxy-(3,4-dihydroxyphenyl)methyl]oxyimino]acetamido]-3-[(E)-3-pyridinio-1-propenyl]-3-cephem-4-carboxylate (Ic)

To a cooled mixture of 7-amino-3-(3-(E)-pyridinio-1-propenyl)-3-cephem-4-carboxylate hydrochloride (IVc) (1.08 g, 2.37 mmol) [for the preparation of compound IVc see: U.S. Pat. No. 4,751,295 issued on 6/14/88 to Oka et al.) and sodium bicarbonate (398 mg, 47.4 mmol) in DMF (17 ml) and water (8.5 ml) was added activated ester IIIa (1.81 g, 2.84 mmol). The mixture was stirred at room temperature for 4 hrs, maintaining pH of the mixture in the range of 5.0 to 7.0 by the addition of sodium bicarbonate. The reaction was quenched by adjusting the pH to 3 with 1N-HCl. The mixture was poured into ice-water and the resulting precipitate was collected by filtration and dried. The solid (3.0 g) was dissolved in TFA (20 ml) and anisole (2 ml) and the solution was left at room temperature for 40 min. The dark brown solution was poured into isopropyl ether (200 ml) and the resulting precipitate was collected by filtration. The crude product was chromatographed on a column of HP-20 (eluent 30% methanol-water) and C18 Bondapak (eluent 8% methanol-water), successively. The desired fractions were pooled and concentrated in vacuo to give 82 mg (6& yield) of the title product, mp 160° C. (dec.).

IR $\nu_{max}$ (KBr) cm$^{-1}$ 3609, 1770, 1668, 1615; UV $\nu_{max}$ (pH 7 phosphate buffer) nm ($\epsilon$) 259 (16,600), 266 (16,900), 288 (21,300); $^1$H NMR (D$_2$O) & 3.18 (1H, d, J=17.3 Hz), 3.46 (1H, d, J=17.3 Hz), 5.10 (1H, d, J=4.6 Hz), 5.33 (2H, br d, J=7.7 Hz), 5.42 (1H, s) 5.71 (1H, d, J=4.6 Hz), 6.12 (1H, dt, J=7.7 & 15.8 Hz), 6.9-7.0 (3H, m), 7.03 (1H, s), 7.04 (1H, d, J=15.8 Hz), 8.09 (2H, dd, J=5.5 & 7.7 Hz), 8.58 ($^1$H, d, J=7.7 Hz), 8.86 (2H, d, J=5.5 Hz); HPLC (column SSC-ODS-262, 254 nm, solvent 10% CH$_3$CN-pH 3.5 buffer, one ml/min): two peaks at 5.20 min & 5.41 min (peak height, ca. 1:1).

EXAMPLE 5

Benzotriazol-1-yl 2-(2-aminothiazol-4-yl)-2-(Z)-[5-t-butoxycarbonyl-2,2-(dimethylbenzodioxol-6-yl)methyl]oxyimino]acetate (XIa)

A solution of 2-(2-aminothiazol-4-yl)-2-[(Z)-[(5-t-butoxycarbonyl-2,2-dimethylbenzodioxol-6-yl)methyl]oxyimino]acetic acid Xa (898 mg, 20 mmol), dicyclohexylcarbodiimide (453 mg, 2.4 mmol) and N-hydroxybenzotriazole (367 mg, 2.4 mmol) in THF (40 ml) was stirred at room temperature for 1 hr. The resulting precipitate was filtered off and the filtrate was concentrated to give activated ester XIa (1.18 g).

IR $\nu_{max}$ (KBr) cm$^{-1}$ 1810, 1695, 1620.

EXAMPLE 6

7-[2-(2-Aminothiazol-4-yl)-2-[(Z)-[(5-t-butoxycarbonyl-2,2-dimethylbenzodioxol-6-yl)methyl]oxymino]acetamido]-3-[(E)-3-pyridinio-1-propenyl]-3-cephem-4-carboxylate (XIIa)

To a cooled suspension of 7-amino-3-[3-(E)-pyridiniol-propenyl]-3-cephem-4-carboxylate hydrochloride IVc.(820 mg, 1.80 mmol) and NaHCO$_3$ (302 mg, 3.60 mmol) in DMF-water (2.1) (18 ml) was added activated ester XIa (1.18 g, 2.0 mmol) and additional NaHCO$_3$ to keep the pH at 6. After 6 hr at room temperature, the pH was brought to 3 with 1N-HCl. The mixture was poured into ice-water and the resulting precipitate was collected by filtration to give 1.99 g of the crude product. The crude product was purified by a column of C-18 Bondapak (eluent 40% MeOH-H$_2$O) to afford 810 mg (60% yield) of the title compound.

IR $\nu_{max}$ (KBr) cm$^{-1}$ 1760, 1660, 1620.

EXAMPLE 7

7-[2-(2-Aminothiazol-4-yl)-2-[(Z)-(2-carboxy-4,5-dihydroxybenzyl)oxyimino]acetamido]-3-[(E)-3-pyridinio-1-propen-1-yl]-3-cephem-4-carboxylate (Id)

A solution of 7-[2-(2-aminothiazol-4-yl)-2-[(Z)-[(5-t-butoxycarbonyl-2,2-dimethylbenzodioxol-6-yl)methyl]oxyimino]acetamido]-3-[(E)-3-pyridinio-1-propenyl]-3-cephem-4-carboxylate XIIa (810 mg, 1.08 mmol) in 90% TFA (10 ml) and anisole (1.0 ml) was stirred at room temperature for 2 hrs. After removal of the volatile materials, the residue was treated with isopropyl ether (50 ml). The obtained crude solid (540 mg) was purified chromatographically by HP-20 (eluent 30-40% MeOH-H$_2$O) to provide 259 mg (37% yield) of the title product, mp 165°C. (dec.).

IR $\nu_{max}$(KBr) cm$^{-1}$ 3410, 1760, 1660, 1625; UV $\nu_{max}$ (pH 7 phosphate buffer) nm ($\epsilon$) 291 (27,700); $1_H$ NMR (D$_2$O+NaHCO$_3$) δ 3.49 & 3.53 (2H, ABq, J=17 Hz), 5.17 (1H, J=5 Hz), 5.34 (2H, br d, J=7.5 Hz), 5.39 (2H, s), 5.75 (1H, d, J=5 Hz), 6.12 (1H, dt, J=7.5 & 16 Hz), 6.89 (1H, d, J=16 Hz), 6.97 (1H, s), 7.03 (1H, s), 7.09 (1H, s), 8.10 (2H, dd, J=7 & 8 Hz), 8.62 (1H, dt, J=1.5 & 8 Hz), 8.88 (2H, d, J=1.5 & 7 Hz). FAB-MS m/z 653 (M+H)+.

EXAMPLE 8

Diphenylmethyl 7-[2-(2-aminothiazol-4-yl)-2-[(Z)-[diphenylmethyloxycarbonyl-(3,4-dihydroxyphenyl)methyl]oxyimino]-acetamido]-3-chloromethyl-3-cephem-4-carboxylate (VIIa)

To a solution of diphenylmethyl 7-amino-3-chloromethyl3-cephem-4-carboxylate (VIa) (685 mg, 1.65 mmol) in THF (8.3 ml) was added benzotriazol-1-yl 2-(2-aminothiazol-4-yl)2-(Z)-(diphenylmethyloxycarbonyl-(3,4-dihydroxyphenyl) methyl]oxyiminoacetate (IIIa) (955 mg, 1.50 mmol) and the mixture was stirred for 5 hr at room temperature. The reaction mixture was diluted with ethyl acetate, washed with water dried over MgSO$_4$ and concentrated under reduced pressure. The crude product was chromatographed on a column of silica gel to afford 566 mg (41% yield) of the title compound.

IR $\nu_{max}$ (KBr) cm$^{-1}$ 1775 1730 1680 1610; $^1$H NMR (CDCl$_3$) δ3.35 (2H, ABq), 4.35 (2H, ABq), 5.00 (1H, d, J=5 Hz), 5.75 (1H, s), 5.95 (1H, dd, J=5 & 7 Hz), 6.5-7.5 (14H, m).

EXAMPLE 9

Diphenylmethyl 7-[2-(2-aminothiazol-4-yl)-2-[(Z)-[diphenylmethyloxycarbonlyl-(3,4-dihydroxylphenyl)methyl]oxyimino]acetamido]-3-iodomethyl-3-cephem-4-carboxylate (VIIIa)

A mixture of diphenylmethyl 7-[2-(2-aminothiazol-4-yl)-2-[(Z)-[diphenylmethyloxycarbonyl-(3,4-dihydroxyphenyl)methyl]oxyimino]acetamido]-3-chloromethyl-3-cephem-4-carboxylate (VIIa) (500 mg, 0.55 mmol) and NaI (248 mg, 1.65 mmol) in acetone (5.5 ml) was stirred for 1 hr at ambient temperature under argon. The reaction mixture was concentrated in vacuo diluted with ethyl acetate, washed with 10% aqueous Na$_2$S$_2$O$_3$ solution, dried over MgSO$_4$ and concentrated to yield 510 mg (92% yield) of iodide VIIIa.

IR $\nu_{max}$ (KBr) cm$^{-1}$ 1770, 1730, 1680, 1615.

EXAMPLE 10

Diphenylmethyl 7-[2-(2-aminothiazol-4-yl)-2-[(Z)-[diphenylmethyloxycarbonyl-(3,4-dihydroxyphenyl)methyl]oxyimino]acetamido]-3-(5,6-diacetoxy-2-methyl-2-isoindolinio)methyl-3-cephem-4-carboxylate iodide (IXa)

To a cooled solution of diphenylmethyl 7-[2-(2-aminothiazol-4-yl)-2-[(Z)-[diphenylmethyloxycarbonyl-(3,4-dihydroxyphenyl)methyl]oxyimino]acetamido-3-iodomethyl-3-cephem-4-carboxylate (VIIIa) (500 mg, 0.50 mmol) in CH$_2$Cl$_2$ (5 ml) and toluene (25 ml) was added a mixture of 5,6-diacetoxy-2-methyl-2-isoindoline (188 mg, 0.75 mmol) and toluene (5 ml) and the mixture was stirred for 1 hr at 0° C. The resulting precipitate was filtered off, washed and dried to give 358 mg (57% yield) of the title product as a tan powder.

IR $\nu_{max}$ (KBr) cm$^{-1}$ 1775, 1680, 1610.

EXAMPLE 11

7-[2-(2-Aminothiazol-4-yl)-2-[(Z)-[carboxy(3,4-dihydroxyphenyl)methyl]oxyimino]acetamido]-3-(5,6-dihydroxy-2-methyl-2-isoindolinio)methyl-3-cephem-4-carboxylate (Ie)

A solution of diphenylmethyl 7-[2-(2-aminothiazol-4-yl) 2-[(Z)-[[diphenylmethyloxycarbonyl-(3,4-dihydroxyphenyl)methyl]oxyimino]acetamido]-3-(5,6-diacetoxy-2-methyl-2-isoindolinio)-3-cephem-4-carboxylate iodide (IXa) (650 mg, 0.52 mmol) in TFA (5 ml) and anisole (0.5 ml) was stirred at room temperature for 1 hr and concentrated in vacuo. The residue was treated with isopropyl ether (50 ml) to give 440 mg of a tan powder. The solid was dissolved in pH 7 phosphate buffer (20 ml) and treated with acetylesterase (1 ml). After stirring for 4 hr at room temperature, the reaction mixture was adjusted to pH 3 with 1N HCl and chromatographed on a column of HP-20. The crude product thus obtained was purified chromatographically with C-18 Bondapak and LH-20 successively to afford 37 mg (10%) of the title compound, mp 166° C. (dec.).

IR $\nu_{max}$ (KBr) cm$^{-1}$ 3420, 1770, 1615; UV $\nu_{max}$ (pH 7 phosphate buffer) nm (ε) 224 (24,300), 220 (15,700, shoulder); $^1$H NMR (D$_2$O+NaHCO$_3$) δ3.17 (3H, s), 3.59 (2H, ABq), 3.76 (3H, s), 4.20 (2H, ABq), 5.04 (1H, d, J=4.8 Hz), 5.40 (1H, s), 5.71 (1H, d, J=4.8 Hz), 6.8-7.1 (6H, m); FAB-MS m/z 713 (M+H)+.

SCHEME A

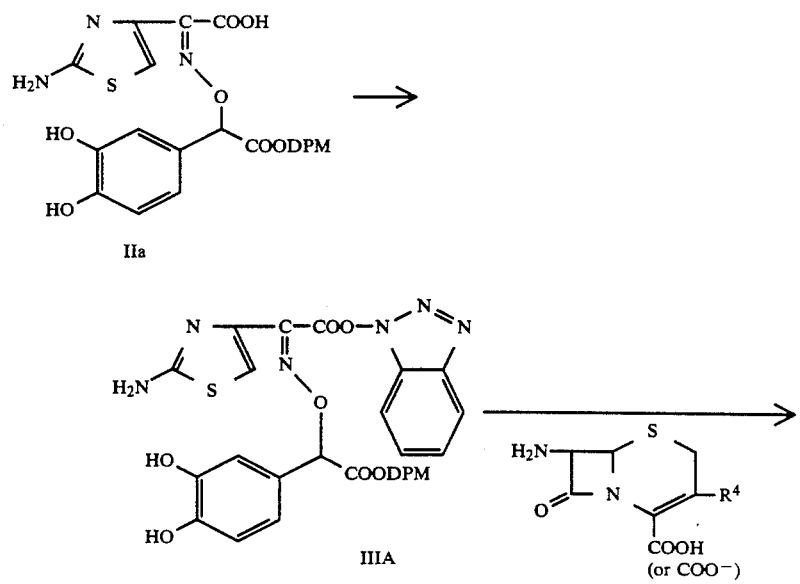

SCHEME A -continued
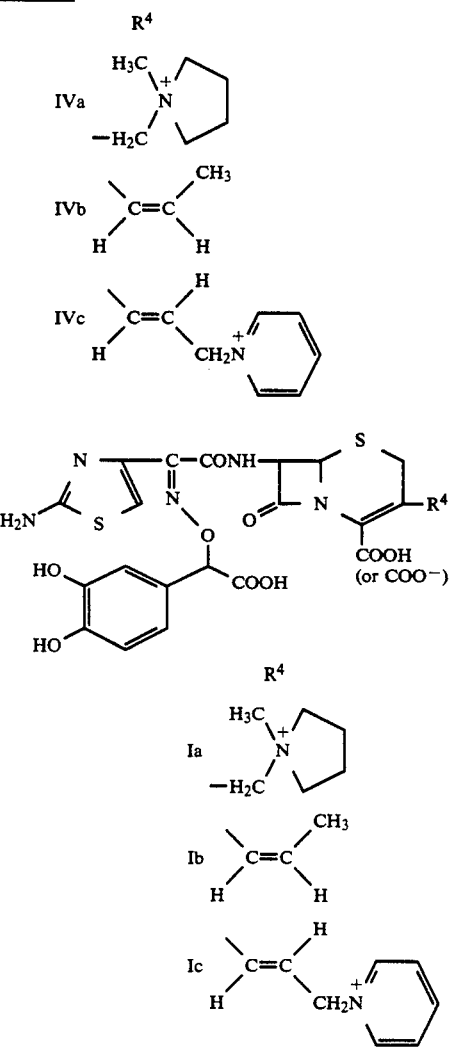
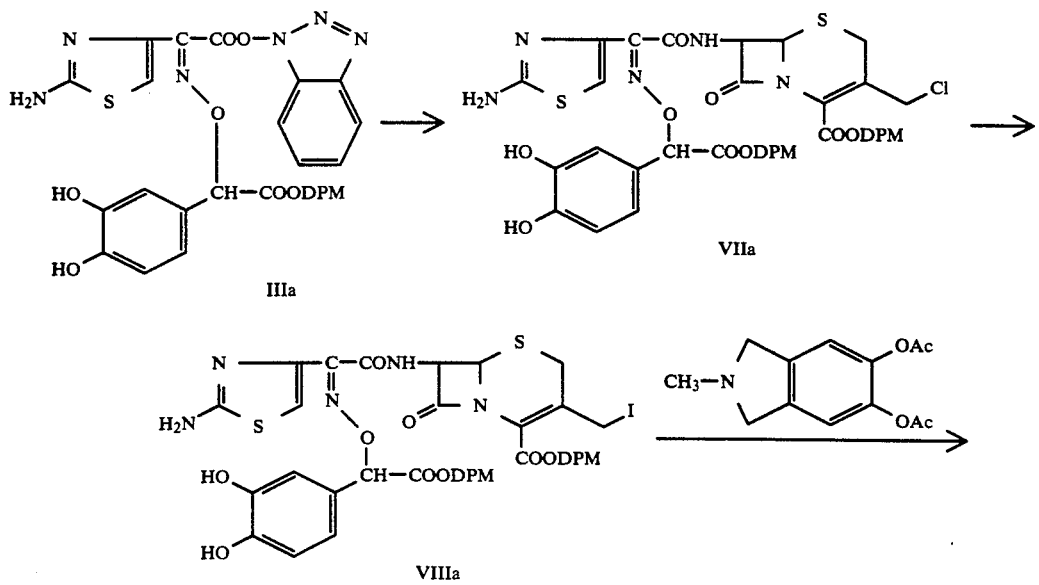

-continued
SCHEME B

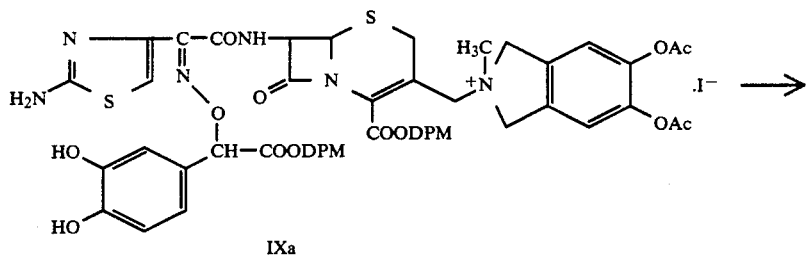

IXa

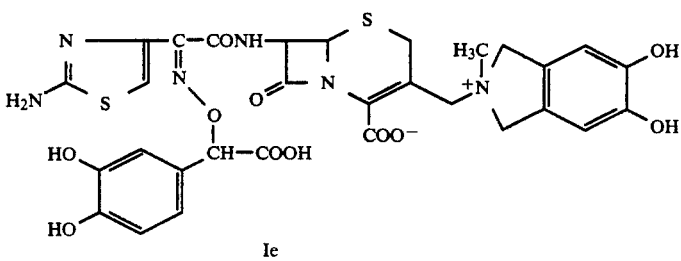

Ie

SCHEME C

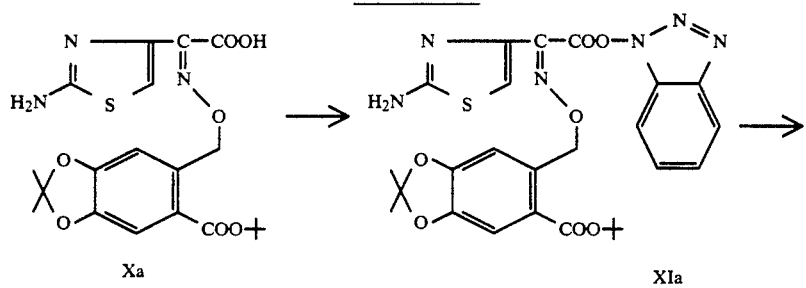

Xa    XIa

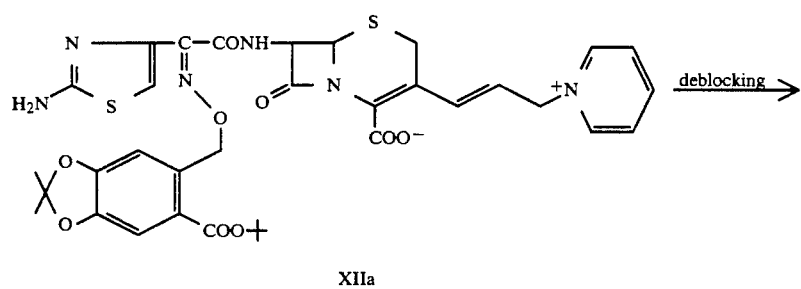

XIIa

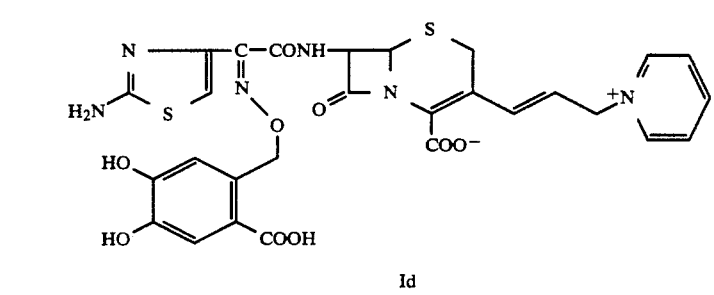

Id

Antibacterial Activity

Minimum inhibitory concentrations (MICs) for the compounds in the above examples were determined against thirty two strains of test organisms by a two-fold serial agar dilution method in Mueller-Hinton agar. Geometric means of MICs were calculated against six groups of the test organisms which are classified as follows and summarized in Table 1.

| Group | Organism |
|---|---|
| Gp-Ia | Penicillin(PC)-sensitive *S. aureus* (5 strains). |

| Group | Organism |
|---|---|
| Gp-Ib | Penicillin(PC)-resistant *S. aureus* (5). |
| Gn-Ia | Cephalothin(CET)-sensitive *E. coli* (2), *Kl. pneumoniae* (1) and *Pr. mirabilis* (2). |
| Gn-Ib | Cephalothin(CET)-resistant *E. coli* (3) and *Kl. pneumoniae* (2). |
| Gn-II | *M. morganii* (1), *Ent. cloacae* (2) and *Ser. marcescens* (2). |
| Gn-III | *Ps. aeruginosa* (7). |

In vivo antibacterial activity was determined against three bacterial infections (*S. aureus* Smith, *E. coli* Juhl and *P. aeruginosa* A9843A) by intramuscular administration to mice just after the bacterial challenge. $PD_{50}$ values are summarized in Table 2 in comparsion with the MIC values against the corresponding organisms.

TABLE 1

In Vitro Activity
Geometric mean of MIC (mcg/ml)

| Compound | Gp-Ia (5 strains) | Gp-Ib (5) | Gn-Ia (5) | Gn-Ib (5) | Gn-II (5) | Gn-III (7) |
|---|---|---|---|---|---|---|
| Ia | 1.4 | 3.1 | 0.30 | 0.40 | 0.80 | 1.6 |
| Ib | 0.92 | 2.1 | 0.17 | 0.35 | 7.3 | 5.1 |
| Ic | 0.26 | 0.4 | 0.076 | 0.15 | 0.46 | 2.3 |
| Id | 0.61 | 1.6 | 0.087 | 0.17 | 0.46 | 0.88 |
| Ie | 8.3 | 13 | 0.46 | 0.46 | 1.6 | 0.30 |

TABLE 2

| | S. aureus Smith | | E. coli Juhl | | P. aeruginosa A9843A | |
|---|---|---|---|---|---|---|
| Compound | $PD_{50}$ (mg/kg, im) | MIC (mcg/ml) | $PD_{50}$ | MIC | $PD_{50}$ | MIC |
| Ia | 5.6 | 1.6 | 0.14 | 0.2 | 6.3 | 1.6 |
| Ib | 6.8 | 0.8 | 1.5 | 0.4 | 17 | 3.1 |
| Ic | 1.4 | 0.4 | 0.067 | 0.05 | 12 | 3.1 |
| Id | 1.0 | 0.8 | 0.017 | 0.10 | 7.2 | 0.80 |
| Ie | 2.4 | 12.5 | 0.045 | 0.8 | 2.1 | 0.4 |

Based on the foregoing biological studies, it can be appreciated that compounds of Formula I are potent antibacterial agents.

What is claimed is:

1. A compound of formula I

I wherein
$R^1$ and $R^2$ are hydrogen or carboxy, with the proviso that both cannot be the same;
$R^3$ is hydrogen or acetyl; and
$R^4$ is a radical of the formula $$-CH=CH-CH_2-R^6$$

in which $R^6$ is hydrogen, a lower $C_{1-3}$ alkyl, or a radical of the formula in which in which n is 1 or 2, and $R^5$ is hydrogen or acetyl;
or a nontoxic pharmaceutically acceptable salt, physicologically hydrolyzable ester or solvate thereof.

2. A compound of claim 1 wherein $R^1$ is carboxy; $R^2$ and $R^3$ are hydrogen; and $R^6$ is hydrogen or 3. The compound of claim 2 wherein $R^4$ is —CH=CH—CH_3.

4. The compound of claim 3 wherein the ethylidene bond in the radical $R^4$ is in the Z configuration.

5. A compound of claim 2 wherein $R^4$ is $$-CH=CH-CH_2-\overset{+}{N}$$

6. The compound of claim 5 wherein the ethylidene bond in the radical $R^4$ is in the E configuration.

7. A compound of claim 1 wherein $R^1$ and $R^3$ are hydrogen; $R^2$ is carboxy.

8. A compound of claim 7 wherein $R^4$ is $$-CH=CH-CH_2-\overset{+}{N}$$

9. The compound of claim 8 wherein the ethylidene bond in the $R^4$ radical is in the E configuration.

10. A pharmaceutical composition comprising an antibacterial effective amount of a compound as claimed in any one of claims 1 to 9 and a pharmaceutically acceptable carrier or diluent.

11. A method for treating bacterial infection in a mammal, which comprises administering to said mammal an antibacterial effective amount of a compound of as claimed in any one of claims 1 to 9.

* * * * *